United States Patent [19]

Manning et al.

[11] 4,386,086

[45] May 31, 1983

[54] METHOD FOR CONTROLLING ECTOPARASITIC ACARINA

[75] Inventors: David T. Manning, Charleston; John A. Durden, South Charleston, both of W. Va.

[73] Assignee: Union Carbide Corporation, Danbury, Conn.

[21] Appl. No.: 936,396

[22] Filed: Aug. 24, 1978

[51] Int. Cl.³ .................... A01N 35/00; A01N 37/34; A01N 43/40; A01N 43/08

[52] U.S. Cl. .................................. 424/244; 424/331; 424/324; 424/317; 424/319; 424/300; 424/304; 424/285; 424/275; 424/320; 424/251; 424/301; 424/309; 424/308; 424/305; 424/312; 424/314; 424/311; 424/310; 424/267; 424/263; 424/274

[58] Field of Search ............... 424/331, 324, 317, 319, 424/300, 304, 285, 275, 320, 251, 301, 309, 308, 305, 312, 314, 311, 310, 244, 267, 263, 274

[56] References Cited

U.S. PATENT DOCUMENTS 3,622,632 11/1971 Holland et al. .................... 424/324
4,104,043 8/1978 Durden et al. .................... 424/312

OTHER PUBLICATIONS

Drummond–USDA Pub. ARS-S-101, pp. 1-5, 46, 55.

Primary Examiner—Frederick E. Waddell
Attorney, Agent, or Firm—Richard C. Stewart; Clement J. Vicari; Dale L. Carlson

[57] ABSTRACT

A method of controlling ectoparasitic Acarina that bore into and through the dermal integument of warm blooded animals by orally administering an 2-aryl-1,3-indandione and derivatives to said animals in an amount sufficient to kill said ectoparasites.

3 Claims, No Drawings

METHOD FOR CONTROLLING ECTOPARASITIC ACARINA

This invention relates to a method of controlling certain ectoparasitic Acarina that bore into and through the dermal integument of warm blooded animals. The method of this invention is carried out by orally administering to the animals a 2-arylindandione compound or its enol derivative in an amount sufficient to kill the ectoparasite.

More particularly, this invention relates to a method of controlling ectoparasitic Acarina that bore into and through the dermal integument of warm blooded animals which comprises orally administering to the animals an effective amount of a compound of the formula:

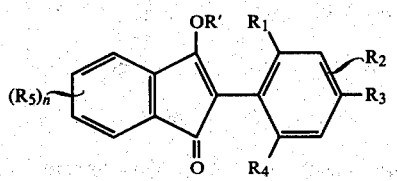

wherein:

$R_1$ is hydrogen, methyl, ethyl, methoxy, ethoxy, fluoro, chloro, bromo, trichloromethyl, trifluromethyl or mixed chlorofluoromethyl;

$R_2$ is hydrogen, lower alkyl, lower haloalkyl, lower alkoxy, acylamido, fluoro, chloro or bromo;

$R_3$ is hydrogen, lower alkyl, lower alkoxy, fluoro, chloro, bromo, nitro, acylamido, trichloromethyl, $R_4$ is methyl, ethyl, methoxy, ethoxy, fluoro, chloro or bromo;

$R_5$ is hydrogen, lower alkyl, lower alkoxy, fluoro, chloro, bromo, trifluoromethyl, trichloromethyl, mixed chlorofluoromethyl or acylamido;

$R_1$ and $R_2$ or $R_4$ and $R_2$ may together form a —CH=CH—CH=CH— and when $R_4$ is ethyl, methoxy or ethoxy; $R_1$, $R_2$ and $R_3$ may not all be hydrogen;

n is a small whole number from 1 to 4;

R' is hydrogen or

wherein $R_6$ is hydrogen, halogen or any organic radical that does not interfere with the hydrolyzability of the ester moiety.

As indicated above, the $R_6$ substituent of the ester moiety may be hydrogen, halogen or essentially any organic radical that does not interfere with the hydrolyzability of the ester moiety including organic radicals having substituents such as halogen, nitro, alkyl, alkoxy, alkyl, thio, keto, cyano, amido, etc. Illustrative of the wide range of permissible $R_6$ functions are:

Alkyl, such as methyl, t-butyl, heptadecyl, pentadecyl, chloroethyl, cyanoethyl, nitropropyl, dibromopropyl and cyanopropyl;

Alkenyl, such as vinyl, allyl and undecenyl;

Alkynyl, such as ethynyl and propynyl;

Bicylcycloalkenyl, such as 2-norbornenyl;

Cycloalkyl, such as cyclopropyl, cyclopentyl, cyclohexyl, cycloheptyl and bicyclooctyl Bicycloalkyl, such as 2-norbornenyl;

Cycloalkenyl, such as cyclopentenyl, cyclohexenyl and methylcyclohexenyl;

Alkylsulfinylalkyl, such as methylalkyl, butylsulfinylethyl and pentylsulfinylmethyl;

Alkylthioalkyl, such as methylthiomethyl, propylthioethyl, butylthioethyl and octylthiomethyl, Alkylsulfonylalkyl, such as nonylsulfonylethyl, ethylsulfonylethyl and butylsulfonylalkyl Alkoxyalkyl, such as isopropoxymethyl, methoxymethyl and propoxyethyl;

Alkoxycarbonylalkyl, such as methoxycarbonylpropyl, cyclohexyloxycarbonylethyl and butoxycarbonylbutyl;

Arylalkyl such as benzyl, chlorobenzyl, nitrobenzyl, 3-phenylpropyl, phenylethyl, and 1-naphthylmethyl Aryloxyalkyl such as phenoxyethyl, dichlorophenoxymethyl, methoxyphenoxyethyl and naphthyloxymethyl;

Arylsulfonylalkyl such as phenylsulfonylmethyl;

Arylsulfinylalkyl such as p-tolylsulfinylethyl;

Arylthioalkyl such as phenylthiomethyl and naphthylthiomethyl;

Aryl such as phenyl, chlorophenyl, nitrophenyl, cyanophenyl, fluorophenyl, methoxyphenyl, trimethylphenyl and chloronaphthyl;

Alkoxy such as methoxy, butoxy, choromethoxy, octyloxy, dodecyloxy and ethylhexyloxy;

Alkylthio such as methylthio, isopropylthio and octylthio;

Aryloxy such as phenoxy and chlorophenoxy;

Heterocyclic such as furyl, thienyl, pyridyl and pyrimidinyl;

Arylthio, such phenylthio, chlorophenylthio and tolythio.

Amino such as dimethylamino, t-butylamino, methylphenylamino, 2,4,6-trimethylphenylamino, and cyclohexylmethylamino. By way of further illustration, the amino substituents can be radicals having the formula —NR$^7$R$^8$, wherein R$^7$ is hydrogen, alkyl, alkenyl, alkynyl, cycloalkyl or aryl and R$^8$ is alkyl, alkenyl, alkynyl, cycloalkyl or aryl or R$^7$ and R$^8$, taken together, form a lower alkylene or lower dialkylene ether linkage.

Acylamidoalkyl such as acetamidomethyl and propionamidoethyl.

Carbomoylalkyl such as carbamoylmethyl and N,N-dimethylcarbamoylethyl.

It is believed, that within broad limits the character of the $R^1$ group has little or no effect upon the biological activity potential of the enol ester composition. It is believed that the function of the ester grouping in the novel compositions of this invention is to facilitate movement of the composition to the proper situs within the pest. The first step in the eventual destruction of the pest is believed to involve hydrolysis of the enol ester to the parent indanedione composition, and, thus, the degree to which the composition is susceptible to hydrolysis plays an important role in its overall biological activity. The $R_6$ group is, therefore, preferably one in which the ester moiety is appropriately hydrolyzable.

All compounds falling within the above generic formula exhibit activity against demodertic mange to a greater or lesser extent. Some exhibit very powerful activity in extremely small dosages while others require larger dosages to be effective.

Activity is greatest in compounds having an alkyl or a halo substituent in an ortho position on the 2-phenyl moiety, especially when the alkyl group is relatively small such as methyl or ethyl and preferably methyl. This is also true of alkoxy substituents and thus methoxy substituents are preferred.

The most active compounds have at least one and preferably both ortho positions of the 2-phenyl moiety substituted with either lower alkyl or halogen. Compounds having no substituents in either ortho position are not preferred because of their effect on blood coagulation.

In general, all of the preferred new compositions are either totally lacking in mammalian toxicity or exhibit only minimal mammalian toxicity.

The following compounds are illustrative of the compounds that are useful in the method of this invention:

3-(3-cyanopropionyloxy)-2-(2',6'-dimethylphenyl)indone
3-(acetamidoacetyloxy)-2-(2'-chloro-4',6'-dimethylphenyl)indone
3-(2-methyl-2-nitropropionyloxy)-2-(2',4',6'-trimethylphenyl)indone
3-(diphenylacetyloxy)-2-(2',6'-dichlorophenyl)indone
3-(4-cyanobenzoyloxy)-2-(2',4',6'-trimethylphenyl)indone
3-(4-methylthiobenzoyloxy)-2-(2'-methyl-6'-ethylphenyl)indone
3-(acetoxy)-2-(2',4'-dimethyl-6'-ethylphenyl)indone
3-(3-methylbutyryloxy)-2-(2'-chloro-6'-ethylphenyl)indone
3-(crotonoyloxy)-2-(2'-bromo-6'-chlorophenyl)indone
3-(2-butynoyloxy)-2-(2'-methoxy-6'-methylphenyl)indone
3-(cyclobutanoyloxy)-2-(2'-bromo-6'-methylphenyl)indone
3-(cyclopent-2-enoyloxy)-2-(2',6'-dibromophenyl)indone
3-(4-bromobutyryloxy)-2-(2',6'-dimethyl-4'-ethylphenyl)indone
3-(2-methylthiopropionyloxy)-2-(2',6'-dichloro-4-methylphenyl)indone
3-(3-ethoxybutyryloxy)-2-(2'-chloro-4',6'-diethylphenyl)indone
3-(3-ethoxycarbonylbutyryloxy)-2-(2'-bromo-6'-fluorophenyl)indone
3-(2-phenylbutyryloxy)-2-(2',6'-dibromo-4'-methylphenyl)indone
3-(3-phenoxypropionyloxy)-2-(2',6'-dichloro-4'-fluorophenyl)indone
3-(phenylthioacetyloxy)-2-(2'-chloro-6'-methylphenyl)indone
3-(benzoyloxy)-2-(2',6'-dimethyl-4'-isopropylphenyl)indone
3-(4-bromobenzoyloxy)-2-(2',4'-dichloro-6'-methoxyphenyl)indone
3-(3-isopropylbenzoyloxy)-2-(2'-methyl-6'-trifluoromethylphenyl)indone
3-(4-ethoxybenzoyloxy)-2-[2'-(t-butyl)-6'-methylphenyl]indone
3-(3,5-dinitrobenzoyloxy)-2-(2',6'-dimethoxy-4'-methylphenyl)indone
3-(formyloxy)-2-(2'-ethyl-6'-methylphenyl)indone
3-(chlorocarbonyloxy)-2-(2',6'-dimethyl-4'-chlorophenyl)indone
3-(isobutyloxycarbonyloxy)-2-(2',4'-dimethyl-6'-chlorophenyl)indone
3-(ethylthiocarbonyloxy)-2-(2'-fluoro-6'-methylphenyl)indone
3-(phenoxycarbonyloxy)-2-(2'-ethoxy-4',6'-dimethylphenyl)indone
3-(phenylthiocarbonyloxy)-(2',6'-dimethyl-4'-trifluoromethylphenyl)indone
3-(N-isopropylcarbamoyloxy)-2-(2',6'-diethylphenyl)indone
3-(N-hexyl-N-ethylcarbamoyloxy)-2-(2'-bromo-6'-ethylphenyl)indone
3-(N-allyl-N-methylcarbamoyloxy)-2-(2',6'-dimethyl-4'-isopropylphenyl)indone
3-(N,N-dicrotylcarbamoyloxy)-2-(2'-methoxy-4',6'-dimethylphenyl)indone
3-(N,N-dipropargylcarbamoyloxy)-2-(2'-methyl-4',6'-diethylphenyl)indone
3-(N-cyclopentyl-N-methylcarbamoyloxy)-2-(2',6'-dimethyl-4'-chlorophenyl)indone
3-[N-(4-methylphenyl)-N-ethylcarbamoyloxy]-2-(2',6'-dimethyl-4'-methoxyphenyl)indone
3-(heptanoyloxy)-2-(2',4',6'-trimethyl-3'-ethylphenyl)indone
3-(2-ethylpentanoyloxy)-2-(2',4'-dimethyl-6'-chloro-3'-methoxyphenyl)indone
3-(3-hexenoyloxy)-2-(2',5'-dichloro-6'-methylphenyl)indone
3-(propioloyloxy)-2-(2',3',6'-trimethylphenyl)indone
3-(cyclopropanoyloxy)-2-(2',6'-dimethyl-3'-chlorophenyl)indone
3-(2-bicyclooct-5-encarbonyloxy)-2-(2',6'-dimethyl-3'-bromophenyl)indone
3-(6-chloroheptanoyloxy)-2-(2',6'-dimethyl-3'-methoxyphenyl)indone
3-(3-propylthiopropionyloxy)-2-(2',6'-dimethyl-3'-fluorophenyl)indone
3-(3-methoxypropionyloxy)-2-(2'-methyl-3'-chloro-6'-methoxyphenyl)indone
3-[3-(butoxycarbonyl)propionyloxy]-2-(2'-methyl-6'-trifluoromethyl-3'-fluorophenyl)indone
3-[(4-chlorophenyl)acetyloxy]-2-(2',6'-dichloro-3'-bromophenyl)indone
3-[2-(2-chloro-4-methylphenoxy)propionyoxy]-2-(2'-ethyl-6'-methyl-3'-chlororphenyl)indone
3-(4-chlorophenylthioacetyloxy)-2-(2',6'-dichloro-3',4'-dimethylphenyl)indone
3-(benzoyloxy)-2-(2',6'-dimethyl-3',4'-dichlorophenyl)indone
3-(2,4,5-trichlorobenzoyloxy)-2-(2',3',4',6'-tetramethylphenyl)indone
3-(3,5-dimethylbenzoyloxy)-2-(2',6'-dichloro-3'-methylphenyl)indone
3-(3,4,5-trimethoxybenzoyloxy)-2-(2',3',4'-trimethyl-6'-methoxyphenyl)indone
3-(4-nitro-3-methylbenzoyloxy)-2-(2',4',6'-trichloro-3'-methylphenyl)indone
3-(formyloxy)-2-(2',3'-diethyl-6'-methylphenyl)indone
3-(chlorocarbonyloxy)-2-(2',4',6'-trimethyl-3'-chlorophenyl)indone
3-(ethoxycarbonylmethylthiocarbonyloxy)-2-(2'-chloro-6'-methylphenyl)indone
3-(allylthiocarbonyloxy)-2-(2',6'-dimethylphenyl)indone
3-(2,4-dichlorophenylthiocarbonyloxy)-2-(2',4'-dimethyl-6'-ethylphenyl)indone
3-[4-(acetamido)phenoxycarbonyloxy]-2-(2',6'-dimethyl-4'-ethyl-3'-chlorophenyl)indone
3-[N,N-di(n-propyl)carbamoyloxy]-2-(2',4',6'-trimethyl-3'-bromophenyl)indone
3-(propionyloxy)-2-(2',4',6'-trimethylphenyl)-5-ethylindone 3-(acetoxy)-2-(2',6'-dichlorophenyl)-5-t-butylindone
3-(2-ethylhexanoyloxy)-2-(2',4',6'-trimethylphenyl)-4,6-dimethylindone
3-(cyclopropanecarbonyloxy)-2-(2',6'-dichlorophenyl)-5,6-dichloroindone
3-[2-ethoxycarbonyl-2-methylpropionyloxy]-2-(2',6'-dichlorophenyl)-4-chloro-5-methylindone
3-(pivaloyloxy)-2-(2',4',6'-trimethylphenyl)-5-bromoindone
3-(2-ethylhexanoyloxy)-2-(2',4',6'-trimethylphenyl)-5,7-dimethylindone
3-(pivaloyloxy)-2-(2',4',6'-trimethylphenyl)-5-fluoroindone
3-(isobutyryloxy)-2-(2',6'-dimethylphenyl)-5-methoxyindone
3-(pivaloyloxy)-2-(2'-trichloromethyl-6'-methylphenyl)indone
3-(isobutyryloxy)-2-(2'-trifluoromethyl-4',6'-dichlorophenyl)indone
3-(acetyloxy)-2-(2',6'-dimethyl-4'-nitrophenyl)indone
3-(propionyloxy)-2-(2',6'-dichloro-4'-acetamidophenyl)indone
3-(butyryloxy)-2-(2'-methyl-4'-trifluoromethylphenyl)indone
3-(pivaloyloxy)-2-(2',6'-dichloro-4'-trichlorophenyl)indone
3-(pivaloyloxy)-2-(2',6'-dichloro-4'-chlorodifluoromethylphenyl)indone
3-(acetyloxy)-2-(2'-dichlorofluoromethyl-4',6'-dichlorophenyl)indone
3-(benzoyloxy)-2-(2',4',6'-trimethyl-3'-formamidophenyl)indone
3-(acetyloxy)-2-(2',4'-dimethyl-5'-trifluoromethylphenyl)indone
3-(butyryloxy)-2-(2',4',6'-trichloro-3'-dichlorofluoromethylphenyl)indone
3-(4-chloronaphthylcarbonyloxy)-2-(2',4',6'-trimethylphenyl)indone
3-(methoxycarbonyloxy)-2-(2'-methylphenyl)indone
3-(propoxycarbonyloxy)-2-(2',6'-diethylphenyl)indone
3-(isopropylthiocarbonyloxy)-2-(2'-chloro-6'-ethylphenyl)indone
3-(methoxyethylthiocarbonyloxy)-2-(2',4',6'-trimethylphenyl)indone
3-(2,4-dimethylphenoxycarbonyloxy)-2-(2',6'-dimethylphenyl)indone
3-(pyrimidin-5-ylcarbonyloxy)-2-(2'-bromophenyl)indone
3-(3-propionamidoethylcarbonyloxy)-2-(2',6'-dichlorophenyl)indone
3-(carbamoylmethylcarbonyloxy)-2-(2',4',6'-trimethylphenyl)indone
3-(N,N-dimethylcarbamoylethylcarbonyloxy)-2-(2'-chloro-6'-bromophenyl)indone
3-(2-nitropropionyloxy)-2-(2'-ethyl-6'-methylphenyl)indone
3-(3-cyanobutyryloxy)-2-(2'-bromo-6'-fluorophenyl)indone
3-(2,3-dibromopropionyloxy)-2-(2',4',6'-trimethylphenyl)indone
3-(acryloyloxy)-2-(2',6'-dimethylphenyl)indone
3-(propioloyloxy)-2-(2'-bromo-6'-methylphenyl)indone
3-(2-norborn-5-enecarbonyloxy)-2-(2',6'-dichlorophenyl)indone
3-(cycloheptanecarbonyloxy)-2-(2'-bromo-6'-methylphenyl)indone
3-(octylthioacetyloxy)-2-(2',6'-dibromophenyl)indone
3-(3-isopropoxypropionyloxy)-2-(2',4',6'-triethylphenyl)indone
3-(3-cyclohexyloxycarbonylpropionyloxy)-2-(2'-bromo-6'-ethylphenyl)indone
3-(3-nitrophenylacetyloxy)-2-(2',6'-dimethylphenyl)indone
3-(1-naphthaleneacetyloxy)-2-(2',4',6'-trimethylphenyl)indone
3-(2-naphthyloxyacetyloxy)-2-(2'-bromophenyl)indone
3-[3-(1-naphthylthio)propionyloxy]-2-(2',4',6'-trimethylphenyl)indone.

Preferred for use in the method of this invention are the compounds in which, $R_1$ is hydrogen, methyl, ethyl, methoxy, fluorine, chlorine or bromine;

$R_2$, $R_3$ and $R_5$ are individually hydrogen, lower alkyl, lower alkoxy, fluorine, chlorine or bromine;

$R_4$ is methyl, ethyl, methoxy, fluorine, chlorine or bromine;

R' is hydrogen or

wherein R is a linear or branched chain alkyl moiety having from 1 to 30 carbon atoms.

Useful compounds are known and can be conveniently prepared for utilizing the methods known to those of skill in the art. The indandione compounds can be prepared by reacting an appropriately substituted benzaldehyde compound with an appropriately substituted phthalide compound as described in U.S. Pat. No. 3,622,632.

The enol ester compounds can be prepared conveniently by the reaction of an indandione with an acid anhydride or acid halide in accordance with the following general reaction scheme:

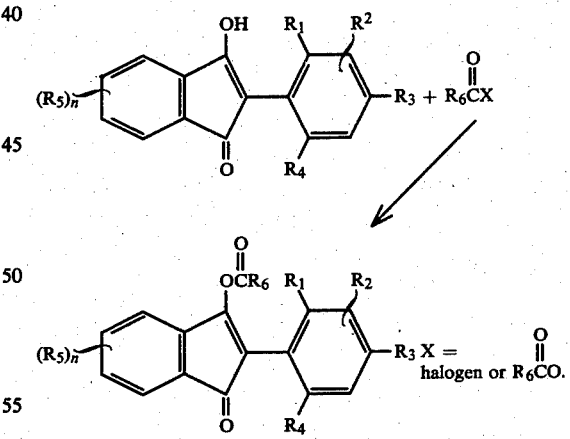

The reaction is preferably carried out in the presence of an acid acceptor such as N,N-dimethylaniline, pyridine, alpha-picoline, any lutidine, collidine or a tertiary aliphatic amine in a suitable solvent such as acetone, chloroform, toluene, dimethylformamide or the like. Inorganic bases such as potassium carbonate may also be employed. The reaction is not temperature sensitive and may be conducted over a broad range to yield the desired product.

The enol ester compositions in which $R_6$ is halogen can be prepared by reacting the appropriate indandione with the appropriate carbonyl halide. Enol ester compositions in which $R_6$ is amino are preferred by reacting the appropriate amine with a 3-halocarbonyloxy substituted indone.

The active compounds used in the method of this invention may, in some instances, be orally administered directly in an undiluted form to the animal to be treated or the active compound may be formulated with a suitable carrier into a composition prior to use. By the term, "suitable" what is meant is that the carrier is chosen, having regard to the active compound employed and the animal being treated so that it will not have any deleterious effect upon the animal being treated, the method of this invention or the results obtained thereby. The carrier can be a solid or a liquid depending on how the composition is applied. It is believed to be within the competence of one skilled in the art to choose the appropriate carrier for a particular compound and a particular application.

Suitable liquid diluents or carriers include water, N-methylpyrrolidone, or other non-toxic liquid carriers with or without surface active agents. Liquid concentrates may be prepared by dissolving one of the active compounds with a carrier that is non-toxic to mammals and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

The active compounds may also be formulated in solid form, such as a tablet, a gel, a cream or the like. In the preparation of solid formulation, the active ingredient is dispersed in and on non-toxic solid materials such as potato starch, lactose, sucrose, corn starch, vaseline, propylene glycol, paraffin, glycerin formal and the like.

Compositions useful in the conduct of the method of this invention may also contain other optional ingredients insofar as they do not interfere with the activity of the compounds toward the Acarina ectoparasite. and are not harmful to the animal being treated.

The precise amount of the compound used will, of course, depend upon a number of factors, including the specific compound employed, the degree of infestation, the intended duration of treatment and the like. However, in general the amount of the active compound used will range from about 0.1 to about 1000 milligrams of active compound per kilogram of animal body weight per day.

The following representative specific examples are presented to more clearly illustrate the methods used to prepare useful compounds and the manner in which they can be used in the method of this invention.

EXAMPLE I

Preparation of
3-(Acetyloxy)-2-(2',4',6'-Trimethylphenyl)Indone

A suspension of 2.64 g (0.01 mole) of 2-(2',4',6'-trimethylphenyl)-1,3-indandione in 50 ml of acetic anhydride was treated with two drops of pyridine. After stirring for three hours the solid had dissolved and the clear solution was concentrated in vacuo at 60°. The residue was taken up in ether, washed with cool potassium bicarbonate solution and water, and the ether solution was dried over magnesium sulfate. Filtration followed by evaporation produced a solid which was recrystallized from hexane to give the desired product, M.P. 115–116.

EXAMPLE II

Preparation of
3-(Isopropyloxycarbonyloxy)-2-(2',4',6'-Trimethylphenyl)Indone

To a mixture of 9.2 g. (0.035 mole) of 2-(2',4',6'-trimethylphenyl)-1,3-indandione, 4.0 g. of pyridine and 200 ml. of hydrocarbon stabilized chloroform, was added dropwise with stirring, 4.3 g. (0.035 mole) of isopropyl chloroformate at 25°–30° C. After the addition was completed the reaction mixture was stirred at room temperature for two days, then added to 200 ml. of 10 percent hydrochloric acid. The mixture was stirred for three minutes and the chloroform layer was separated and washed two times with water, then dried with magnesium sulfate. The chloroform was removed in vacuo and the yellow oily residue was dissolved in n-hexane and treated with charcoal for 10 minutes. This mixture was filtered and the filtrate concentrated to a crystalline residue which was recrystallized from isopropanol to give 10 g. of a yellow solid. M. P. 95°–96° C.

EXAMPLE III

Preparation of
2-(2',4',6'-Trimethylphenyl)-3-(Pivaloyloxy)Indone

To a stirred slurry of 2128 g. (8.6 moles) of 2-(2',4',6'-Trimethylphenyl)-1,3-indandione in 8000 ml of isopropyl ether was added 1420 g. (18 moles) of dry pyridine followed by 1089 g. (9 moles) of pivaloyl chloride. When addition of the pivaloyl chloride was complete the reaction mixture was heated at reflux for 0.5 hour and, after cooling, the resulting solution was extracted with 2×2000 ml of water, 1×1000 ml of 50-volume percent hydrochloric acid, and again with water. Concentration of the isopropyl ether solution in vacuo produced, in three successive fractions, 2792 g. (93.2 percent) of product, M. P. 105°–106°.

EXAMPLE IV

Preparation of
3-(2-Ethylhexanoyloxy)-2-(2',4',6'-Trimethylphenyl)Indone

A mixture of 520 grams (2.0 moles) of 2-(2',4',6'-trimethylphenyl)-1,3-indandione 2 liters of toluene and 212 grams (2.1 moles) of triethylamine was stirred at room temperature for one hour after which 325 grams (2.0 moles) of 2-ethylhexanoyl chloride was added with stirring at 30° to 40° (with some cooling) over a period of 20 minutes. The resulting deep red mixture was stirred at 30° to 35° for three hours and then at room temperature overnight.

The by-product triethylamine hydrochloride was collected and washed with toluene. The combined filtrates were washed with 10 percent hydrochloric acid and then with water until neutral. After drying over magnesium sulfate, the toluene solution was concentrated to produce a solid residue which was recrystallized from hexane with charcoal treatment. There was obtained 580 grams (75.2 percent) of product, M. P. 65°–67° C.

EXAMPLE V

Preparation of 3-Stearoyloxy-2-(2',4',6'-Trimethylphenyl)Indone

To a solution of 66 g. (0.25 mole) of 2-(2',4',6'-trimethylphenyl)-1,3-indandione, 22 g. of pyridine and 600 ml. of hydrocarbon stabilized chloroform was added dropwise with stirring at 25°–30° C., 76 g. (0.25 mole) of stearoyl chloride. After the addition was completed, the reaction mixture was stirred for 20 hours at 28° C. The mixture was then added to 500 ml. of 10 percent hydrochloric acid and stirred for five minutes. The chloroform layer was separated and washed two times with water then with 300 ml. of 5 percent potassium bicarbonate and finally washed until neutral with water. The organic layer was dried with magnesium sulfate, and then the chloroform was removed in vacuo. The yellow oily residue was dissolved in n-hexane and allowed to stand at 28° C. for three hours while a small amount of solid separated (starting 2-(2',4',6'-trimethylphenyl)-1,3-indandione). This was removed and the filtrate concentrated to a very viscous oily residue which was treated with n-hexane and cooled to −10° C. The resulting crystalline solid was filtered and washed with cold n-hexane to give 108 g., M. P. 31°–32° C.

EXAMPLE VI

Preparation of 3-(2-Ethylhexyloxycarbonyloxy)-2-(2',4',6'-Trimethylphenyl)Indone To a solution of 9.2 g. (0.035 mole) of 2-(2',4',6'-trimethylphenyl)-1,3-indandione, 4.0 g. of pyridine, and 200 ml. of hydrocarbon stabilized chloroform was added dropwise with stirring 6.8 g. (0.035 mole) of 2-ethylhexyl chloroformate at 25°–30° C. After the addition was completed, the reaction mixture was stirred at 25°–30° C. for two days, then added to 200 ml. of 10 percent hydrochloric acid. The chloroform layer was separated and washed two times with water, then dried with magnesium sulfate. The chloroform was stripped from the product under reduced pressure. The yellow oily residue was dissolved in 200 ml. of n-hexane and allowed to stand at 25° C. for three hours while a small amount of 2-(2',4',6'-trimethylphenyl)-1,3-indandione separated. This solid was removed and the filtrate was treated with charcoal. The charcoal was removed by filtration and the filtrate was concentrated under reduced pressure (1.0 mm at 28°–30° C.). The product was a yellow oily residue (10 g.).

EXAMPLE VII

Preparation of 3-(4-Chlorobutanoyloxy)-2-(2',4',6'-Trimethylphenyl)Indone

4-Chlorobutyrylchloride 4.9 g. (0.035 mole) was added dropwise with stirring at 25°–32° C. to a solution of 9.2 g. (0.035 mole) of 2-(2',4',6'-trimethylphenyl)-1,3-indandione, 4.0 g. of pyridine and 200 ml. of hydrocarbon stabilized chloroform. After the addition was completed, the mixture was stirred at 28° C. for two days, then added to 200 ml. of 10 percent hydrochloric acid, and stirred for two minutes. The chloroform layer was separated and washed two times with water, then dried with magnesium sulfate. The chloroform was removed from the product under reduced pressure. The resulting solid residue was recrystallized from isopropanol to give 11 g. of a yellow solid. M. P. 98°–100° C.

EXAMPLE VIII

Preparation of 3-Benzoyloxy-2-(2',6'-Dichlorophenyl)Indone

A stirred solution of 2-(2',6'-dichlorophenyl)-1,3-indandione (3.84 g., 0.0132 mole) in 13 ml. of pyridine was treated with benzoyl chloride (1.4 g., 0.01 mole) at room temperature. After the addition was completed the mixture was stirred at room temperature for 16 hours and then poured into dilute hydrochloric acid. The precipitated solid was collected by filtration and then dissolved in ether. The ether solution was washed with dilute hydrochloric acid and then with water (3×50 ml.). The dried ($M_gSO_4$) ether solution was evaporated under reduced pressure to furnish a solid residue which was recrystallized from ethanol to give 1.7 g. (33%) of 3-benzoyloxy-2-(2',6'-dichlorophenyl)indone, M. P. 154°–156° C.

EXAMPLE IX

Preparation of 3-(2-Methylbenzoyloxy)-2-(2',4',6'-Trimethylphenyl)Indone

A mixture of 2-(2',4',6'-trimethylphenyl)-1,3-indandione (7.92 g. 0.03 mole) and o-toluoyl chloride (5.1 g., 0.033 mole) in 30 ml. of pyridine was stirred at room temperature for 20 hours. The mixture was poured into 300 ml. of 10% hydrochloric acid. The oil which separated was extracted with ether and the ether extract was washed with water (2×75 ml.). The dried ($M_gSO_4$) ether solution was evaporated under reduced pressure and the residue thus obtained was recrystallized from ethanol to afford 7.6 g. (66%) of product, M. P. 116°–118° C.

EXAMPLE X

Preparation of 3-(3-Nitrobenzoyloxy-2-(2',6'-Dichlorophenyl)Indone

A mixture of 2-(2',6'-dichlorophenyl)-1,3-indandione (8.73 g., 0.03 mole) and m-nitrobenzoyl chloride (6.12 g., 0.033 mole) in 30 ml. of pyridine was stirred at room temperature for 20 hours. The mixture was added to 300 ml. of 10% hydrochloric acid, and the precipitated solid was collected by filtration. Recrystallization from ethanol afforded 8.0 g. (61%) of the title compound, m. p. 182°–185° C.

EXAMPLE XI

Preparation of 2-(2',4',6'-Trimethylphenyl)-3-Chlorocarbonyloxyindone

To a solution of 25 grams (0.25 mole) of phosgene in 200 ml of benzene was added with stirring at 25° C. a solution of 26 grams (0.1 mole) of 2-(2',4', 6'-trimethylphenyl)-1,3-indandione and 14 grams (0.11 mole) of N,N-dimethylaniline in 200 ml of benzene over a ten minute period. The resulting mixture was stirred at 35° for eight hours and then filtered. The resulting filtrate was concentrated in vacuo and the yellow residual oil was taken up in hexane and left overnight. After filtering, the hexane solution was concentrated in vacuo to a residue which crystallized. After washing with cold hexane and drying this crystalline residue amounted to 25 grams (77 percent yield), M. P. 95°–97°. The infrared spectrum (Nujol) was consistent with the desired compound showing bonds at (μ): 5.6 (ClC(O)O—); 5.78 (keto C═O), 6.03 (C═C); 6.19 and 6.21 (arom. C═C), 8.9 (C—O— of ester); 11.25 (isolated arom. H); 13.1 (4adj. arom. H). The nmr spectrum (CDCl₃) showed the following bands (δ, ppm); 2.18, 2.22 (two singlets, ratio 2:1; 3 arom. CH₃, 9H); 6.92 (singlet, isol. arom. H, 2H); 7.02–7.62 (complex mult., arom. H, 4H).

EXAMPLE XII

Preparation of 2-(2',4', 6'-Trimethylphenyl)-3-N-(t-Butyl)Carbamoyloxyindone

To a solution of 12 grams (0.038 mole) of 3-chlorocarbonyloxy-2-(2',4',6'-trimethylphenyl) indone in 150 ml of toluene was added dropwise with stirring at ambient temperature, 5.6 grams (0.076 mole) of t-butylamine. After stirring for one hour at room temperature the reaction mixture was filtered and the filtrate concentrated in vacuo to produce a yellow oily residue. This was dissolved in ethyl ether, and, after a thorough water wash, the ether solution was dried over magnesium sulfate, treated with charcoal and finally filtered. This filtrate was concentrated in vacuo to give a solid residue which was recrystallized from isopropyl alcohol to provide 8 grams (63.8 percent) of product, M. P. 145°–147°; ir., Nujol (μ): 2.98 (NH); 5.61 (enol CO); 5.9 (keto CO), 6.02 (conj. C═C); 6.22 (arom. C═C); 7.21, 7.23 (t-C(CH₃)₃); 8.9 (C—O—); nmr, CDCl₃ (δ, ppm): 1.19 (singlet, C(CH₃)₃, 9H); 2.18, 2.24 (pair of singlets, ratio 2:1, arom. CH₃, 9H); 5.4 (broad singlet, NH, 1H); 6.89 (singlet, isol. arom. H. 2H); 7.0–7.6 (complex mult., 4 arom. H, 4H).

EXAMPLE XIII

Preparation of 2-(2',4',6'-Trimethylphenyl)-3-(4-Morpholino)Carbonyloxyindone

Using the same procedure used in Example XII above, but substituting 6.6 grams (0.076 mole) of morpholine for t-butylamine, there was obtained as a residual yellow solid, 11 grams (77 percent), M. P. 43°–47°. The infrared spectrum was consistent with proposed structure.

EXAMPLE XIV

Preparation of 2-(2',4',6'-Trimethylphenyl)-3-(2,4-Dimethylallophanoyloxy) Indone To a mixture of 9.2 grams (0.035 mole) of 2-(2',4',6'-trimethylphenyl)-1,3-indandione and 200 ml of toluene was added 4 grams (excess) of triethylamine and the resulting mixture was stirred at ambient temperature for 30 minutes. To this stirred mixture was then added 5.3 grams (0.035 mole) 2,4-dimethylallophanoyl chloride and the resulting solution was heated at 45° for four hours after which the mixture was cooled and filtered. The filtrate was washed 4 times with water, dried over magnesium sulfate, and finally concentrated in vacuo to a residue which was dissolved in hexane and treated with charcoal. Removal of the hexane in vacuo produced a residual oil which was taken as product, 10 grams (75.5 percent yield); ir. (capillary) (μ): 2.95 (NH); 5.75 (enol carbamate C═O); 5.80 (ketone (C═O); 5.83 (shoulder —NHC(O)N); 6.09 (enol C═C); 6.25 (arom. C═C), 8.9/7.8 C—O—).

EXAMPLE XV

Preparation of Bis[2-(2',4',6'-Trimethylphenyl)Indon-3-yl]Carbonate

To a solution of 20 grams of phosgene in 200 ml of toluene was added dropwise with stirring at ambient temperature a solution of 26 grams (0.1 mole) of 2-(2',4',6'-trimethylphenyl)-1,3-indandione and 12 grams (0.12 mole) of triethylamine in 200 ml of toluene. The mixture was stirred at room temperature for two hours and was then concentrated to about one-half volume. The remaining solution was washed twice with cold water and then dried over magnesium sulfate. Filtration and subsequent concentration of the filtrate in vacuo produced a yellow solid, 20 grams (72 percent yield), M. P. 221°–223°. The infrared and nmr spectra are consistent with the proposed structure.

EXAMPLE XVI

Preparation of 3-Acetoxy-2(2',6'-Dichlorophenyl)-4(and 7-)Methylindone

To a solution of 3.05 gram (0.01 mole) of 2-(2',6'-dichlorophenyl)-4-methyl-1,3-indandione in 50 ml of acetic anhydride was added 3 drops of pyridine and the resulting yellowish solution was stirred at room temperature for three hours. The mixture was then concentrated in vacuo to a solid residue which was taken up in ether, and the resulting solution was washed with ice water and then dilute sodium bicarbonate solution and finally dried over magnesium sulfate. Filtration and subsequent concentration of the filtrate in vacuo to produce a yellow crystalline residue which was crystallized from isopropyl ether to yield 2.3 grams (66.2 percent) of product, M. P. 101°–120°. The infrared and nmr spectra were consistent with the desired structure. These, together with the elemental analysis, show the material to be a mixture of the isomers indicated in the title of this Example.

The physical properties of other compounds that are useful in the conduct of the method of this invention and that can be prepared by the procedures of Examples I to XVI are set forth in Table I below.

TABLE I

| Name | M.P.°C. or IR |
|---|---|
| 3-Benzoxyloxy-2-(2',4',6'-trimethylphenyl)indone | 147–150 |
| 3-(2-Chlorobenzoyloxy)-2-(2',4',6'-trimethylphenyl)indone | 108–110 |
| 3-(3-Chlorobenzoyloxy)-2-(2',4',6'-trimethylphenyl)indone | 140–142 |
| 3-(4-Chlorobenzoyloxy)-2-(2',4',6'-trimethylphenyl)indone | 93–95 |
| 3-(2-Methylbenzoyloxy)-2-(2',4',6'-trimethylphenyl)indone | 116–118 |
| 3-(3-Methylbenzoyloxy)-2-(2',4',6'-trimethylphenyl)indone | 115–117 |
| 3-(4-Methylbenzoyloxy)-2-(2',4',6'-trimethylphenyl)indone | 113–116 |
| 3-(3-Methoxybenzoyloxy)-2-(2',4',6'-trimethylphenyl)indone | 112–115 |
| 3-(4-Methoxybenzoyloxy)-2-(2',4',6'-trimethylphenyl)indone | 117–120 |
| 3-(3-Nitrobenzoyloxy)-2-(2',4',6'-trimethylphenyl)indone | 123–126 |
| 3-(4-Nitrobenzoyloxy)-2-(2',4',6'-trimethylphenyl)indone | 165–167 |

TABLE I-continued

| Name | M.P.°C. or IR |
|---|---|
| 3-(2,4-Dichlorobenzoyloxy)-2-(2',4',6'-trimethylphenyl)-indone | 126–128 |
| 3-(3,4-Dichlorobenzoyloxy)-2-(2',4',6'-trimethylphenyl)-indone | 157–159 |
| 3-(3,5-Dichlorobenzoyloxy)-2-(2',4',6'-trimethylphenyl)-indone | 165–168 |
| 3-(2,6-Dichlorobenzoyloxy)-2-(2',4',6'-trimethylphenyl)-indone | 168–172 |
| 3-(2,3,6-Trichlorobenzoyloxy)-2-(2',4',6'-trimethylphenyl)-indone | 163–165 |
| 3-(2,6-Dimethoxybenzoyloxy)-2-(2',4',6'-trimethylphenyl)-indone | 141–143 |
| 3-(2,4-Dimethylbenzoyloxy)-2-(2',4',6'-trimethylphenyl)-indone | 118–120 |
| 3-(2,4,6-Trimethylbenzoyloxy)-2-(2',4',6'-trimethylphenyl)-indone | 154–155 |
| 3-(2,6-Dimethylbenzoyloxy)-2-(2',4',6'-trimethylphenyl)-indone | 123–125 |
| 3-(Benzoyloxy)-2-(2',6'-dichlorophenyl)indone | 154–156 |
| 3-(2-Chlorobenzyloyloxy)-2-(2',6'-dichlorophenyl)indone | 106–108 |
| 3-(3-Chlorobenzoyloxy)-2-(2',6'-dichlorophenyl)indone | 124–126 |
| 3-(4-Chlorobenzoyloxy)-2-(2',6'-dichlorophenyl)indone | 113–116 |
| 3-(2-Methylbenzoyloxy)-2-(2',6'-dichlorophenyl)indone | Residue* Product |
| 3-(3-Methylbenzoyloxy)-2-(2',6'-dichlorophenyl)indone | 138–141 |
| 3-(4-Methylbenzoyloxy)-2-(2',6'-dichlorophenyl)indone | 136–140 |
| 3-(3-Methoxybenzoyloxy)-2-(2',6'-dichlorophenyl)indone | 143–145 |
| 3-(4-Methoxybenzoyloxy)-2-(2',6'-dichlorophenyl)indone | 149–152 |
| 3-(3-Nitrobenzoyloxy)-2-(2',6'-dichlorophenyl)indone | 182–195 |
| 3-(4-Nitrobenzoyloxy)-2-(2',6'-dichlorophenyl)indone | 164–167 |
| 3-(2,4-Dichlorobenzoyloxy)-2-(2',6'-dichlorophenyl)indone | 138–140 |
| 3-(3,4-Dichlorobenzoyloxy)-2-(2',6'-dichlorophenyl)indone | 130–132 |
| 3-(3,5-Dichlorobenzoyloxy)-2-(2',6'-dichlorophenyl)indone | 125–130 |
| 3-(2,6-Dichlorobenzoyloxy)-2-(2',6'-dichlorophenyl)indone | 182–185 |
| 3-(2,3,6-Trichlorobenzoyloxy)-2-(2',6'-dichlorophenyl)indone | 210–214 |
| 3-(2,6-Dimethoxybenzoyloxy)-2-(2',6'-dichlorophenyl)indone | 226–228 |
| 3-(2,4-Dimethylbenzoyloxy)-2-(2',6'-dichlorophenyl)indone | 152–154 |
| 3-(2,4,6-Trimethylbenzoyloxy)-2-(2',6'-dichlorophenyl)indone | 142–145 |
| 3-(2,6-Dimethylbenzoyloxy)-2-(2',6'-dichlorophenyl)indone | 150–152 |
| 2-(2',6'-Dichlorophenyl)-3-(pivaloyloxy)indone | 133–135 |
| 2-(2'-Bromophenyl)-3-(pivaloyloxy)indone | 91–98 |
| 3-Acetoxy-2-(2'-bromophenyl)indone | 93–97 |
| 3-(2-Ethylhexanoyloxy)-2-(2'-fluorophenyl)indone | λ max (μ): 5.61 (ester C=O); 5.8 (ketone C=O); 6.1 (enol C=C) |
| 2-(2'-Chlorophenyl)-3-(pivaloyloxy)indone | 80–82 |
| 2-(2'-Chlorophenyl)-3-(2-methylpentanoyloxy)indone | λ max (μ): 5.62 (ester C=O); 5.8 (ketone C=O); 6.1 (enol C=C) |
| 2-(2'-Chlorophenyl)-3-(stearoyloxy)indone | 50–53 |
| 2-(2'-Chloro-6'-methylphenyl)-3-(pivaloyloxy)indone | 93–96 |
| 2-(2'-Methylphenyl)-3-(pivaloyloxy)indone | 62 |
| 3-(2-Ethylhexanoyloxy-2-(2'-methylphenyl)indone | λ max (μ): 5.65 (enol ester); 5.81 (ketone C=O); 6.11 (enol C=C) |
| 2-(2'-Methylphenyl)-3-(palmitoyloxy)indone | 34–36 |
| 2-(2'-Methylphenyl)-3-(neodecanoyloxy)indone (mixture of isomers) | λ max (μ): 5.62 (ester C=O); 5.79 (ketone C=O); 6.1 (enol C=C) |
| 2-(2',4'-Dimethylphenyl)-3-(stearoyloxy)indone | λ max (μ): 5.6 (ester C=O); 5.79 (ketone C=O); 6.1 (enol C=C) |
| 2-(2',4'-Dimethylphenyl)-3-(lauroyloxy)indone | λ max (μ): 5.6 (ester C=O); 5.79 (ketone C=O), 6.1 (enol C=C) |
| 2-(2',4'-Dimethylphenyl)-3-(2-methylpentanoyloxy)-indone | λ max (μ): 5.62 (ester C=O); 5.79 (ketone C=O); 6.13 (enol C=C) |
| 2-(2',6'-Dimethylphenyl)-3-(pivaloyloxy)indone | 82–84 |

TABLE I-continued

| Name | M.P.°C. or IR |
|---|---|
| 2-(2',5'-Dimethylphenyl)-3-(neodecanoyloxy)indone (mixture of isomers) | λ max (μ): 5.63 (ester C=O); 5.8 (ketone C=O); 6.1 (enol C=C) |
| 2-(2',5'-Dimethylphenyl)-3-(2-ethylbutanoyloxy)-indone | λ max (μ): 5.65 (ester C=O); 5.8 (ketone C=O); 6.1 (enol C=C) |
| 2-(2',5'-Dimethylphenyl)-3-(tridecanoyloxy)indone | λ max (μ): 5.6 (ester C=O); 5.8 (ketone C=O); 6.1 (enol C=C) |
| 2-(2'-Ethyl-6'-methylphenyl)-3-(pivaloyloxy)indone | 69-70 |
| 2-(2',6'-Diethylphenyl)-3-(pivaloyloxy)indone | 98-99 |
| 2-(2',6'-Dimethyl-4'-t-butylphenyl)-3-(pivaloyloxy)-indone | 129-133 |
| 2-(2',6'-Dimethyl-4'-methoxyphenyl)-3-(pivaloyloxy)-indone | 123-124 |
| 3-(Pivaloyloxy)-2-(6'methoxy-2',3',4'-trimethylphenyl)-indone | 108-110 |
| 3-(2-Ethylhexanoyloxy)-2-(1-Naphthyl)indone | λ max (μ): 5.67 (ester C=O); 5.81 (ketone C=O); 6.15 (enol C=C) |
| 3-(Acetoxy)-4(7)-methyl-2-(2',6'-dichlorophenyl)-indone | 101-120 |
| 2-(2',6'-Dichlorophenyl)-4(7)-methyl-3-(pivaloyloxy)-indone | 152-154 |
| 2-(2',6'-Dichlorophenyl)-5(6)-methyl-3-(pivaloyloxy)-indone | 158-160 |
| 2-(2',4',6'-Trimethylphenyl)-3-(acetoxy)indone | 115-116 |
| 2-(2',4',6'-Trimethylphenyl)-3-(propionyloxy)indone | 109-110.5 |
| 2-(2',4',6'-Trimethylphenyl)-3-(isobutyryloxy)indone | 78-80 |
| 2-(2',4',6'-Trimethylphenyl)-3-(pivaloyloxy)indone | 100-102 |
| 2-(2',4',6'-Trimethylphenyl)-3-(2-ethylhexanoyloxy)indone | 66-68 |
| 2-(2',4',6'-Trimethylphenyl)-3-(cyclohexanoyloxy)indone | 62-65 |
| 2-(2',4',6'-Trimethylphenyl)-3-(neodecanoyloxy)indone (mixtures of isomers) | λ max (μ): 5.62 (ester C=O); 5.78 (ketone C=O); 6.1 (enol C=C) |
| 2-(2',4',6'-Trimethylphenyl)-3-(Isopropoxycarbonyloxy)indone | 95-96 |
| 2-(2'4',6'-Trimethylphenyl)-3-(octadecanoyloxy)indone | 34 |
| 2-(2',4',6'-Trimethylphenyl)-3-(methylthioacetoxy)indone | 98-100 |
| 2-(2',4',6'-Trimethylphenyl)-3-(3-methoxycarbonylpropionyloxy)indone | λ max (μ): 5.60 (enol ester C=O); 5.78 (ketone and ester (C=O); 6.08 (enol C=C) |
| 2-(2',4',6'-Trimethylphenyl)-3-(4-chlorobutyryloxy)indone | 98-100 |
| 2-(2',4',6'-Trimethylphenyl)-3-(methoxyacetoxy)indone | 115-117 |
| 2-(2',4',6'-Trimethylphenyl)-3-(endo-exo norborn-5-en-2-carbonyloxy)indone | λ max (μ): 5.62 (enol ester C=O); 5.79 (ketone C=O); 6.09 (enol C=C) |
| 2-(2',4',6'-Trimethylphenyl)-3-(phenylacetoxy)indone | λ max (μ): 5.59 (enol ester C=O); 5.79 (ketone C=O); 6.09 (enol C=C) |
| 2-(2',4',6'-Trimethylphenyl)-3-(dimethylcarbamoyloxy)indone | 117-119 |
| 2-(2',4',6'-Trimethylphenyl)-3-(dodecanoyloxy)indone | λ max (μ): 5.59 (enol ester C=O); 5.79 (ketone C=O); 6.09 (enol C=C) |
| 2-(2',4',6'-Trimethylphenyl)-3-(undec-9-enoyloxy)indone | λ max (μ): 5.61 (enol ester (C=O); 5.81 (ketone C=O); 6.09 (enol C=C) |
| 2-(2',4',6'Trimethylphenyl)-3-(octyloxycarbonyloxy)indone | λ max (μ): 5.60 (enol ester (C=O); 5.79 (ketone C=O); 6.09 (enol C=C) |
| 2-(2',4',6'-Trimethylphenyl)-3-(dodecyloxycarbonyloxy)indone | λ max (μ): 5.61 (enol ester (C=O); 5.80 (ketone C=O); 6.10 (enol C=C) |
| 2-(2',4',6'-Trimethylphenyl)-3-(2-ethylhexyloxycarbonyloxy)indone | λ max (μ): 5.61 (enol ester C=O); 5.79 (ketone C=O); 6.09 (enol C=C) |

TABLE I-continued

| Name | M.P.°C. or IR |
|---|---|
| 2-(2',4',6'-Trimethylphenyl)-3-(octadecyloxycarbonyloxy)indone | 43–45 |
| 2-(2',4',6'-Trimethylphenyl)-3-(octylthiocarbonyloxy)indone | λ max (μ): 5.65 Sh (enol ester C=O); 5.78 (ketone C=O); 6.08 (enol C=C) |
| 2-(2',4',6'-Trimethylphenyl)-3-(cyclopent-2-en-1-ylacetoxy)indone | λ max (μ): 5.60 (enol ester C=O); 5.80 (ketone (C=O); 6.08 (enol C=C) |
| 2-(2',4',6'-Trimethylphenyl)-3-butyryloxy)indone | 78–80 |
| 2-(2',4',6'-Trimethylphenyl)-3-(pentanoyloxy)indone | 67–79 |
| 2-(2',4',6'-Trimethylphenyl)-3-(2-furoyloxy)indone | 153–155 |
| 2-(2',4',6'-Trimethylphenyl)-3-(2-thenoyloxy)indone | 151–153 |
| 2-(2',4',6'-Trimethylphenyl)-3-(3.pyridinecarbonyloxy)-indone | 110–112 |
| 2-(2',4',6'-Trimethylphenyl)-3-(chlorocarbonyloxy)indone | 95–97 |
| 2-(2',4',6'-Trimethylphenyl)-3-(4-chlorophenyloxy carbonyloxy)indone | 97–98 |
| 2-(2',4',6'-Trimethylphenyl)-3-(N—(t-butyl)carbamoyloxy)indone | 145–157 |
| 2-(2',4',6'-Trimethylphenyl)-3-(N—butyl-N—methylcarbamoyloxy)indone | λ max (μ): 5.82 (enol ester C=O); 5.88 (ketone C=O); 6.07 (enol C=C) |
| 2-(2',4',6'-Trimethylphenyl)-3-(N,N—di(butyl)carbamoyloxy)indone | λ max (μ): 5.84 (enol ester C=O); 5.88 (ketone C=O); 6.19 (enol (C=C) |
| 2-(2',4',6'-Trimethylphenyl)-3-(N—methyl-N—phenylcarbamoyloxy)indone | 120–122 |
| 2-(2',4',6'-Trimethylphenyl)-3-(4-(morpholino)carbonyloxy)indone | 43–47 |
| 2-(2',4',6'-Trimethylphenyl)-3-(piperdinocarbonyloxy)indone | λ max (μ): 5.76 (enol ester C=O); 5.82 (ketone C=O; 6.10 (enol C=C) |
| 2-(2',4',6'-Trimethylphenyl)-3-(N—(2,4,6-Trimethylphenyl)-carbamoyloxy)indone | 152–155 |
| 2-(2',4',6'-Trimethylphenyl)-3-(N—cyclohexyl-N—methylcarbamoyloxy)-indone | λ max (μ): 5.62 (enol ester C—O); 5.85 (ketone C=O); 6.12 (enol C=C) |
| 2-(2',4',6'-Trimethylphenyl)-3-(2,4-dichlorophenoxyacetoxy)indone | 113–115 |
| 2-(2',4',6'-Trimethylphenyl)-3-(3-(2-(2,4,6-trimethylphenyl)-indon)yloxycarbonyloxy)indone | 221–223 |
| 2-(2',4',6'-Trimethylphenyl)-3-(2,4-dimethylallophanoyloxy)indone | λ max (μ): 5.71 (enol ester C=O); 5.8 (ketone C=O); 6.09 (enol C=C) |
| 3-(2-Ethylhexanoyloxy)-2-phenyl-indone | λ max (μ): 5.61 (ester C=O); 5.8 (ketone C=O); 6.12 (enol C=C) |
| 2-Phenyl-3-(stearoyloxy)indone | 63–64 |
| 2-Phenyl-3-(pivaloyloxy)indone | 102–104 |
| 2-Phenyl-3-(acetoxy)indone | 114–116 |
| 2-Phenyl-3-(benzoyloxy)indone | 168–169 |
| 2-(4'-Chlorophenyl)-3-(pivaloyloxy)indone | 114–116 |
| 3-(2-ethylbutanoyloxy)-2-(4'-isopropylphenyl)-indone | λ max (μ): 5.63 (ester C=O); 5.8 (ketone C=O); 6.15 (enol C=C) |
| 2-(4'-isopropylphenyl)-3-(pivaloyloxy)indone | 84–87 |
| 2-(4'-isopropylphenyl)-3-(palmitoyloxy)indone | λ max (μ): 5.59 (ester C=O); 5.8 (ketone C=O); 6.13 (enol C=C) |
| 2-(2'-Ethylphenyl)-3-pivaloyloxy-indone | λ max (μ): 5.51, 5.68 (ester C=O) 5.81 (ketone C=O); 6.12 enol C=C) |
| 2-(2'-isopropylphenyl)-3-pivaloyloxy-indone | λ max (μ): 5.5, 5.63 (ester C=O) 5.80 (ketone C=O); 6.11 (enol C=C) |
| 2-(2',6'-diisopropyl)phenyl-3-pivaloyloxy-indone | 168–171 |
| 3-(2-Ethylhexanoyloxy)-2-(2'-methoxyphenyl-indone | λ max (μ): 5.5, 5.67 (ester C=O) 5.82 (ketone C=O); 6.1 (enol C=C) |

TABLE I-continued

| Name | M.P.°C. or IR |
| --- | --- |
| 2-(2'-Methoxyphenyl)-3-(neodecanoyloxy)-indone | λ max (μ): 5.5, 5.62 (ester C=O) 5.79 (ketone C=O); 6.1 (enol C=C) |
| 2-(2'-Methoxyphenyl)-3-(pivaloyloxy)-indone | 90–92 |
| 2-(2'-Trifluoromethylphenyl)-3-pivaloyloxy indone | 82–84 |

*Calcd for $C_{22}H_9Cl_5O_3$; C, 67.65; H, 3.45; Found C, 67.03; H, 3.72
λ max: 5.7μ (ester C=O); 6.1μ (enol double bond); 5.82μ (ketone C=O); 8.2μ (C—O stretch).

The following Examples illustrate the utility of the method of this invention in the control of Acarina ectoparasite that bore into the bodies of warmblooded animals.

EXAMPLE XVII

Use of 2-(2',4',6'-Trimethylphenyl)-3-Pivaloyloxyindone in the Control of Demodectic Mange

Example

A mixed breed dog (sire: Weimaraner, dam: English Springer Spaniel), age 10 months and weighing 50–60 pounds was diagnosed as a case of demodectic mange. The subject was treated with daily topical applications (to the lesions) with either a liquid formulation of isobornyl thiocyanoacetate ("Fungisarc") or a dispersion of the title compound in vaseline. When these treatments proved to have no effect, a total of 4.5 to 5.0 grams of pure 2-(2',4',6'-trimethylphenyl)-3-pivaloyloxyindone was administered orally over a 9–14 day period by incorporation of 321–555 mg increments of the compound into the regular daily diet. Treatment was ceased following the 4.5–5.0 gram total dose due to vomiting. Topical application of "Fungisarc" was resumed but was discontinued within a week when it was noticed that the skin lesions had disappeared.

Example

Use of 2-(2',4',6'-Trimethylphenyl)-3-Acetoxyindone in the Control of Demodectic Mange Various species of dogs infected with demodectic mange were orally administered test formulations of 2-(2',4',6'-trimethylphenyl)-3-acetoxyindone. Tablets of the test formulation were prepared either by direct compression or wet granulation with 110 ml of absolute ethanol per 400 g of powder. The composition of these tablets is as follows:

| | Tablet Composition | |
| --- | --- | --- |
| | Component | Quantity |
| (a) | 2-(2',4'6'-Trimethyl-phenyl)-3-Acetoxyindone | 200 mg |
| (b) | Corn starch or potato starch | 30 mg |
| (c) | Sodium lauryl sulphate | 1.5 mg |
| (d) | Magnesium stearate | 3 mg |
| (e) | Lactose | 65.5 mg |

The resulting tablet was then fed into the affected dog. The results are set forth in Table I, below.

TABLE II

Results of Treatment of Demodicosis During Ten Days

| No. | Breed | Body Weight | Daily Dosage | Four-Five Weeks | Remarks |
| --- | --- | --- | --- | --- | --- |
| 1. | Beagle | 14 kg | 7.8 mg/kg | recovered | |
| 2. | Gordon Setter | 21 kg | 15 mg/kg | recovered | |
| 3. | Bouvier | 40 kg | 15 mg/kg | recovered | |
| 4. | Spaniel | 8 kg | 25 mg/kg | recovered | retreated after three weeks |
| 5. | Alsatian | 32 kg | 14 mg/kg | moderate | |
| 6. | Great Dane | 40 kg | 15 mg/kg | moderate | |

It will be understood that the ectoparasite species employed in the above tests is merely representative of a wide variety of ectoparasites that can be controlled by the method of this invention.

The method of this invention is useful for controlling ectoparasites of the order Acarina that bore into the bodies of warmblooded animals. Representative of such ectoparasites are those belonging to the family Demodicidal, such as the hog follicle mite (*Demodex phylloides*); the dog follicle mite (*Demodex Canis*) and cattle follicle mite (*Demodex bovis*) and the ear mange mite (*Otodectes cynotic, charisoptes Cunnicali* and others); the family Sarcoptidae, such as itch or mange mite (*Sarcoptes scabiei*) and scaly-leg mite (*Cunnidocoptes mutans*); and the family Psorptidae, such as scab mite (*Psoroptes equi*), sheep scab mite (*Psoroptes equi ovis*).

The ectoparasite that can be controlled by the method of this invention normally affect warmblooded animals. Representative of animals that affected are domestic animals such as, horses, cattles, sheep, chickens, dogs, goats, hogs and the like.

What is claimed is:

1. A method of controlling ectoparasitc Acarina selected from the group consisting of Demodicidae, Sarcoptidae and Psorptidae that bore into and through the dermal integument of warmblooded animals which comprises orally administering to a said animal a said Acarina ectoparasitically effective amount of a compound of the formula:

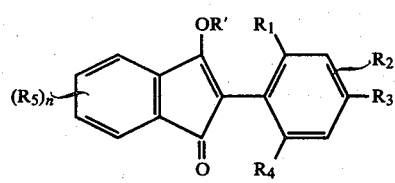

wherein:

$R_1$ is hydrogen, methyl, ethyl, methoxy, ethoxy, fluoro, chloro, bromo, trichloromethyl, trifluoromethyl, or mixed chlorofluoromethyl;

$R_2$ is hydrogen, lower alkyl, lower haloalkyl, lower alkoxy, acylamido, fluoro, chloro or bromo;

$R_3$ is hydrogen, lower alkyl, lower alkoxy, fluoro, chloro, bromo, nitro, acylamido, trichloromethyl, trifluoromethyl or mixed chlorofluoromethyl;

$R_4$ is methyl, ethyl, methoxy, ethoxy, fluoro, chloro, or bromo;

$R_1$ and $R_2$ or $R_4$ and $R_2$ may together form a —CH=CH—CH=CH—chain, and when $R_4$ is ethyl, methoxy or ethoxy; $R_1$, $R_2$ and $R_3$ may not all be hydrogen;

n is a small whole number from 1 to 4;

$R_5$ is hydrogen, lower alkyl, lower alkoxy, fluoro, chloro, bromo, trifluoromethyl, trichloromethyl, mixed chlorofluoromethyl or acylamido;

$R'$ is hydrogen or

$$-CR_6,$$

wherein $R_6$ is hydrogen, halogen or an unsubstituted or substituted organic radical selected from the group consisting of alkyl, alkenyl, alkynyl, cycloalkyl, cycloalkenyl, bicycloalkyl, bicycloalkenyl, alkylthioalkyl, alkylsulfinylalkyl, alkylsulfonylalkyl, alkoxyalkyl, alkoxycarbonylalkyl, arylalkyl, aryloxyalkyl, arylthioalkyl, aryl, alkylaryl, alkoxyaryl, arylsulfinylalkyl, alkoxy, alkylthio, aryloxy, arylthio, arylsulfonyl, alkyl, heterocyclic, acylamido, alkylcarbamoyloxy or amino radicals of the formula:

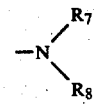

wherein:

$R_7$ is hydrogen, alkyl, alkenyl, alkynyl, cycloalkyl, or aryl and $R_8$ is alkyl, alkenyl, alkynyl, cycloalkyl or aryl or $R_7$ and $R_8$ together may form a lower alkylene or lower dialkylene ether linkage, wherein the permissible substituents are one or more halo, nitro or cyano groups.

2. A method according to claim 1 wherein: said ectoparasitic Acarina is a Demodicidae or Sarcoptidae.

3. A method according to claim 1 wherein: said ectoparasitic Acarina is a Demodicidae.

* * * * *